US006262062B1

(12) United States Patent
Clemens

(10) Patent No.: US 6,262,062 B1
(45) Date of Patent: Jul. 17, 2001

(54) METHOD OF TREATING THE SYNDROME OF CORONARY HEART DISEASE RISK FACTORS IN HUMANS

(75) Inventor: Anton H. Clemens, Madison, WI (US)

(73) Assignee: CPD, LLC, Madison, WI (US)

( * ) Notice: Subject to any disclaimer, the term of this patent is extended or adjusted under 35 U.S.C. 154(b) by 0 days.

(21) Appl. No.: 09/639,061

(22) Filed: Aug. 15, 2000

(51) Int. Cl.[7] .................................................. A61K 31/44
(52) U.S. Cl. ............................................................ 514/282
(58) Field of Search ............................................. 514/282

(56) References Cited

U.S. PATENT DOCUMENTS

| 4,055,175 |   | 10/1977 | Clemens et al. . |         |
|-----------|---|---------|------------------|---------|
| 4,272,540 | * | 6/1981  | Razdan et al.    | 424/260 |
| 4,451,470 | * | 5/1984  | Ganti            | 424/260 |
| 4,478,840 | * | 10/1984 | Smith, Jr.       | 424/260 |
| 4,511,570 |   | 4/1985  | Tuttle .         |         |
| 4,619,936 | * | 10/1986 | Balkanyi et al.  | 514/282 |
| 4,857,533 |   | 8/1989  | Sherman et al. . |         |
| 4,863,928 |   | 9/1989  | Atkinson et al. .|         |
| 4,877,791 |   | 10/1989 | Sherman .        |         |
| 4,880,813 |   | 11/1989 | Frost .          |         |
| 4,882,335 |   | 11/1989 | Sinclair .       |         |
| 4,994,466 |   | 2/1991  | Sherman .        |         |
| 5,086,058 | * | 2/1992  | Sinclair et al.  | 514/282 |
| 5,356,900 |   | 10/1994 | Bihari et al. .  |         |
| 5,468,755 |   | 11/1995 | Cincotta et al. .|         |
| 5,626,860 |   | 5/1997  | Cincotta et al. .|         |
| 5,727,570 |   | 3/1998  | Clemens .        |         |
| 5,878,750 |   | 3/1999  | Clemens .        |         |
| 6,026,817 |   | 2/2000  | Clemens .        |         |

OTHER PUBLICATIONS

The Merck Index 10th Ed., 1983 p. 491–492.
The Merck Index 14th Ed., 1996 p. 1052 [Metyrosine].
R. Landgraf et al.; "Prolactin: A Diabetogenic Hormone", Diabetologia 13, 1977, pp. 99–104, 1976.
The Pharmacological Basis of Therapeutics, Seventh Edition (Chapter 18, p. 383), 1985.
Atkinson et al., "Effects of Long–Term Therapy with Nultrexone on Body Weight in Obesity" Clin. Pharmacol. Ther. 10/85: pp. 419–422.
J.R. Givens et al.; "Reduction of Hyperinsulinemia" J. Clin. Endocr. & Metab. 64/2, 1987, pp. 377–382.
G. R. Van Loon et al.; Endocrinology; vol. 109, p. 46, 1981.
R. Vink et al.; "K–Opioid Antagonist Improves Cellular Bioenergetics and Recovery After Traumatic Brain Injury" Am. J. Physiol. 261, 1991.
Sohel et al. "Influence of Adrenergic Blockers and Antilipemic Agents on Pharmacodynamic Actions of Morphine in Carbon Tetrachloride–Treated Rats." Toxicol Appl Pharmacol 27(3):477–483, Mar., 1974.
Stern et al. "Lack of Awareness and Treatment of Hyperlipidemia in Type II Diabetes in a Community Survey." JAMA 262 (3);360–4, Jul., 1989.
Herz A. "Bidirectional Effects of Opioids in Motivational Processes and the Involvement of D1 Dopamine Receptors." NIDA Res Monogr 1988;90:17–26.
Herz A.; "Opioid Reward Mechanisms: A Key Role in Drug Abuse?" Can J Physiol Pharmacol 76, 3:252–8, 1998.
Pan Z.Z.; "mu–Opposing Actions of the Kappa–Opioid Receptor" Thrends Pharmacol Sci; 19, 3: 94–8, 1998.
Porotoghese, et al.; "Binaltorphimine and Nor–Binal Torphimine, Potent and Selective k–Opioid Receptor Antagonists" Life Sciences 40: 1287–92, 1987.
Jones et al.; Journal of Medicinal Chemistry 41, 25: 4911–4, 1998.
Merz et al.; Advances in biochemical psychopharmacology, vol. 8:91–107, 1974.
Porotoghese et al.; "TENA, A Selective Kappa Opioid Receptor Antagonist" Life Sciences 36:801–5, 1984.
Lewis J.W.; "Buprenorphine" Drug and Alcohol Dependence; 14:363–372, 1985.
McQuay J.J. et al.; "Clinical Effects of Buprenorphine During and After Operation" Br. J. Anaesth; 52:1013–19, 1980.
Ruppin H.; "Loperamide—A Potent Antidiarrhoeal Drug with Actions Along the Alimentary Tract" Aliment Pharmacol Ther 1987, 1(3): 179–190.
Caldara R. et al.; "Effect of Loperamide, a Peripheral Opiate Agonist, on Circulating Glucose, Free Fatty Acids, Insulin, C–Peptide and Pituitary Hormones in Healthy Man" Eur J. Clin Pharmacol; 21, 3:185–8, 1981.
Buzi F. et al.; "Loperamide Test: a Simple and Highly Specific Screening Test for Hypercortisolism in Children and Adolescents" Acta Paediatr; 86, 11: 1177–80, 1997.
Foss et al.; "Restoration of Glucose Homeostasis in Insulin–Dependent Diabetic Subjects"; Diabetes, 31:46–52, 1982.
Pfeifer et al.; "Insulin Secretion in Diabetes Mellitus"; The American Journal of Medicine, 70:579–588, 1981.
Felber et al.; "Effect of a 3–Day Fast on Glucose Storage and Oxidation in Obese Hyperinsulinemic Diabetics; Metabolism," 30,2; 184–189 and Diabetologia, 20:39–44, 1981.
Edelman, S.V.; "Prescribing Oral Antidiabetic Agents: General Considerations"; Clinical Diabetes 16,1:37–40, 1998.

* cited by examiner

Primary Examiner—Raymond Henley, III
(74) Attorney, Agent, or Firm—Michael Best & Friedrich

(57) ABSTRACT

A method of treating a human suffering from one or more conditions included within the Coronary Heart Disease Risk Factor (CHDRF) syndrome. The method includes administering, by a pharmaceutically effective mode, a drug composition having an active ingredient which is selected from opiate antagonists, opiates having $\mu$ agonist activity and combinations thereof.

42 Claims, 1 Drawing Sheet

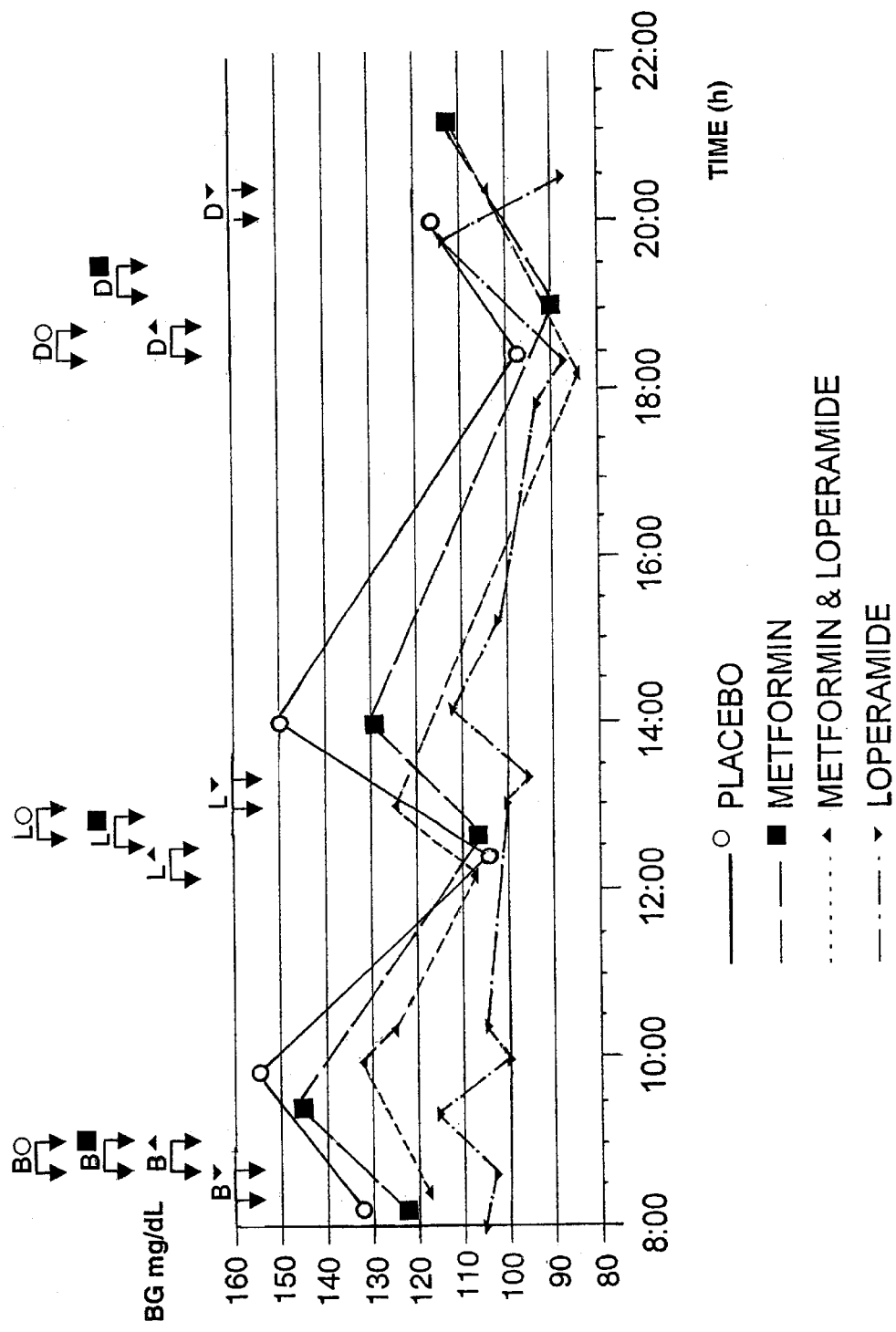

METHOD OF TREATING THE SYNDROME OF CORONARY HEART DISEASE RISK FACTORS IN HUMANS

BACKGROUND OF THE INVENTION

Coronary Heart Disease Risk Factors (CHDRFs) are major causes of death in the industrialized world. CHD risk factors include Type 2 Diabetes (and its precursor, Impaired Glucose Tolerance (IGT)), hyperlipidemia or dislipidemia, overweight, obesity and essential hypertension, i.e., a form of hypertension that occurs without a discoverable organic cause. The CHDRF syndrome may, therefore, be defined as a group of interrelated disorders: Type 2 Diabetes, IGT, Dislipidemia, Overweight, Obesity and essential hypertension. It has also become apparent that Type 2 Diabetes, by itself, represents a syndrome of various, in part sequential, disease states which interact with other components of the CHDRF syndrome. However, the exact interrelationships between the disease states that make up these syndromes is not fully understood. A wide variety of chemical and physical abnormalities associated with these syndromes exist. They include elevations in fasting blood glucose and gluconeogenesis in spite of significant increases in fasting insulin and C-peptide concentrations and increases in lipogenesis. Typically associated with lipogenesis are increases in levels of fasting Free Fatty Acid (FFA), fasting triglycerides (TG) and total cholesterol concentrations, increases in levels of fasting Low Density Lipoprotein (LDL)-cholesterol, decreases in levels of fasting High Density Lipoprotein (HDL)-cholesterol, an increased LDL/HDL ratio, increases in body weight and increases in systolic and diastolic blood pressure.

Although these syndromes are interrelated and typically result from derangements in nutrient metabolism, all the associated symptoms may not be present in individual patients. Accordingly, in some patients lipid metabolism problems may predominate, while in others, carbohydrate metabolism problems may be predominant. While these factors, which lend one aspect of the syndrome to dominate over another, are not well understood, it is clear that each portion of the syndrome, or combinations of portions of the syndrome, represents risk factors in coronary heart disease.

Insulin Resistance/Type 2 Diabetes/CHDRF Syndrome

A common denominator in the etiology of the syndromes of Type 2 Diabetes and the CHDRFs appears to be Insulin Resistance (IR). IR is characterized as a state in which a normal amount of insulin produces a subnormal biological response in carbohydrate metabolism. This may be the case for subjects afflicted with the non-insulin-dependent diabetes form of Type 2 Diabetes and in pre-diabetic subjects affected by Impaired Fasting Glucose (IFG) or Impaired Glucose Tolerance (IGT). These subjects require (and endogenously produce) higher than normal levels of insulin to compensate for their insulin resistance and to normalize their blood glucose levels. Traditionally, IR has been expressed as the insulin/glucose ratio (I/G). More recently, several more complex models have been proposed to define Insulin Resistance or the Insulin Sensitivity Index. Only recently have other biological functions of insulin become the focus of more intense scientific interest, e.g. the role of insulin in endogenous lipogenesis. Although an interaction between insulin resistance and the CHDRF components has been established, the cause and effect relationship between insulin resistance, obesity, dislipidemia and IGT/Type 2 Diabetes is still subject to debate. IR increases FFA levels, which further contributes to IR, thereby creating a vicious circle. Therapeutic modalities for lowering any one of the lipid fractions in dislipidemia have not proven capable of correcting the entire hyperlipidemic complex with a single therapeutic agent.

Compared to Type 1 (juvenile) Diabetes, the Type 2 Diabetes syndrome, particularly its non-insulin-dependent mellitus (NIDDM) forms, is characterized by relatively inadequate endogenous insulin concentrations. However, insulin concentrations in Type 2 diabetics may, in fact, be higher than in the normal population. A possible explanation for this apparent discrepancy is that Type 2 diabetics, as well as subjects afflicted with IFG or IGT, typically require more insulin to control their blood sugar levels. Temporary increases in certain diabetogenic mediators, such as glucagon, growth hormones and catecholamines may initially cause the requirement for more insulin. These mediators communicate their specific control functions as agonists to target tissue or cells through compatible cell bound receptors. Continued, long term agonist load eventually leads to 'down-regulation' of such receptors, i.e. the receptor response and/or sensitivity are decreased. Depending on the agonist involved, this mechanism can lead to tolerance or addiction. As a result, increasing doses are required to achieve the same effect. Antagonists have equivalent receptor specificity as their agonist counterparts, but do not convey any agonist-type control message. In contrast to agonists, prolonged exposure of such receptors to their specific antagonists can restore receptor response or sensitivity, a process called receptor 'up-regulation'.

As long as any agonists load by mediators, such as hormones, neuro-transmitters or neuro-modulators prevails for infrequent, short durations, the respective receptors for such mediators can 'up-regulate' between such temporary agonist loads. In other words, the receptors can resume their normal sensitivity between 'receptor-ligand' interactions. The early stage of IR may be characterized by temporary increases in diabetogenic mediators such as catecholamines and/or glucagon. However, resistance to the action of insulin on the control of glucose may not carry over to the action of insulin on lipogenesis. Even though the individual is resistant to the action of insulin in controlling glucose, the response of lipid metabolism to insulin may remain at the normal level. As temporary agonist 'loads' become more frequent or sustained, the affected receptors will down-regulate. As a result, IR may become a permanent metabolic burden and, with additional diabetogenic factors, such as cortisol, may accelerate progressive increases in hepatic gluconeogenesis (GNG) and glucose production (GP). The IR dependent insulin excess in the face of hyper-gluconeogenesis caused hyperglycemia then becomes a blueprint for hyper- or dislipidemia, overweight and obesity. Gradually, the β-cells' secretory capacity to produce and secrete insulin will diminish, resulting in a slow but steady rise in fasting glucose levels until, eventually, such secretory capacity will be exhausted, at which time the subject becomes 'insulin dependent', i.e. dependent on exogenous insulin injections.

Dislipidemia

Dislipidemia is characterized by any of the following, and combinations thereof: elevated levels of total and LDL-cholesterol, elevated levels of TG, a high LDL/HDL ratio and elevated levels of FFA and low levels of HDL-cholesterol. Lipid metabolism is rather complex. While it is clear that dislipidemia is associated with the development of coronary heart disease, there is no clear understanding of the pathogenic causes and pathways leading up to the manifestation of the various lipid disorders. The relative roles of lipid ingestion versus endogenous lipogenesis in the etiology of lipid abnormalities have not been fully understood.

Overweight/Obesity

Obesity is a disease of major proportions and severe economic consequences. No longer is obesity considered merely a physical or cosmetic inconvenience. Obesity is second only to cigarette smoking as a preventable cause of premature death, and its complications add in excess of $100 billion to U.S. health care costs. Obesity can not be treated effectively by willpower alone, and currently available pharmaceutical drugs are only marginally effective. Moreover, several obesity drugs have recently been withdrawn from the market because of their risk of potentially fatal side-effects, e.g. pulmonary hypertension or heart defects in connection with dexfenfluramin or fenfluramine.

Six out of ten people (approximately 130 million) in the United States are overweight, close to 90 million are obese and 22 million are clinically, morbidly obese.

The definitions of obesity and overweight are somewhat arbitrary. The symptoms of overweight or obesity are characterized by excessive body fat, i.e. the body contains a level of fat beyond that considered normal. Body weight in relationship to height and build is used as a surrogate measure of obesity and overweight. Being 20% over the standard height weight tables is considered obese. The body mass index (BMI) is commonly used in defining normal weight. The BMI is calculated by dividing a subject weight in kilograms by the square of height in meters ($kg/m^2$) or ($lbs.\times 705/inches^2$). A BMI of 25 is considered normal, a BMI of 26–29 is considered overweight, a BMI of 30–40 is obese, and a BMI >40 is considered morbid. A therapeutic intervention is considered effective if it produces a weight reduction of >10%, or a reduction by >5% if 'co-morbid' factors are also improved, e.g. any of the blood analyte concentrations related to IGT, Type 2 Diabetes or dislipidemia.

Despite the recognized interaction between the various CHD risk factors, the pharmaceutical modalities currently available to treat the symptoms of Type 2 Diabetes generally have had no beneficial effect on hyper- or dislipidemia; in fact, some of the medicines widely used to treat Type 2 Diabetes, e.g. sulfonylureas, tend to increase hyperlipidemia and may, therefore, further contribute to overweight and obesity, thereby increasing the CHD risk. Conversely, medicines presently available to treat various forms of hyper- or dislipidemia have little or no impact on IFG, IGT, Type 2 Diabetes, overweight or obesity.

Moreover, no single pharmaceutical agent has been able to treat and correct the entire complex of hyper- or dislipidemia. Drugs such as clofibrate/gemfibrozil can lower TG levels, but have little or no effect on FFA levels, and no effect on total cholesterol levels. Other drugs may shift the proportion of cholesterol found in the form of low and high density lipoprotein cholesterol. For example, certain drugs may actually increase already elevated levels of low density lipoprotein cholesterol. On the other hand, drugs like lovastatin lower the levels of both total and low density lipoprotein cholesterol, while only slightly increasing the level of high density lipoprotein cholesterol. However, these drugs have no effect on FFA and little or no effect on TG levels.

As a result, it is desirable to provide an improved method for treating the syndrome of coronary heart disease risk factors. A new method for treating the early morning rise in hepatic gluconeogenesis and endogenous glucose production is also desired. In other words, an improved method of treatment is desired that lowers high glucose levels resulting from rises in gluconeogenesis and glucose production, and impaired insulin secretion in patients afflicted with CHD risk factors in humans. A new method is also desired wherein the administration of a drug composition does not require a priming dose.

SUMMARY OF THE INVENTION

The present invention provides a method of treating a human suffering from one or more conditions included within the CHDRF syndrome comprising administering, by a pharmaceutically effective mode, a drug composition having an active ingredient which is selected from opiate antagonists, opiates having $\mu$ agonist activity and combinations thereof.

The invention also provides a method for treating elevated fasting glucose levels in individuals, which results from increased gluconeogenesis and glucose production, and impaired insulin secretion, all associated with CHD risk factors.

The invention also provides a method to restore first phase insulin release, and this invention does not require a priming dose.

Other features and advantages of the invention will become apparent to those skilled in the art upon review of the following detailed description and claims.

Before embodiments of the invention are explained in detail, it is to be understood that the invention is not limited in its application to the details of the composition and concentration of components set forth in the following description. The invention is capable of other embodiments and of being practiced or being carried out in various ways. Also, it is understood that the phraseology and terminology used herein is for the purpose of description and should not be regarded as limiting.

The patents, references and articles cited herein are fully incorporated by reference.

BRIEF DESCRIPTION OF DRAWINGS

FIG. 1 is a graph showing the daily blood glucose profile of a 71-year subject afflicted with Type 2 Diabetes and dislipidemia after four different treatments. The four different treatments are described in the detailed description. The blood glucose (BG) of the subject was measured in mg/dL over several time intervals measured in hours (h).

DETAILED DESCRIPTION OF THE INVENTION

As used herein, the terms "opioids," "opioid agonists," "opiate agonists," "opiates having agonist activity" and "agonists" are meant to refer to substances, natural or synthetic, that bind to centrally and/or peripherally located opioid receptors to produce an agonist action.

As used herein, the terms "opiates having $\mu$ agonist activity," "opioids having $\mu$ agonist activity" and "$\mu$ agonists" are meant to refer to substances, natural or synthetic, that bind to the $\mu$ receptor to produce an agonist action.

As used herein, the terms "opioid antagonists," "opiate antagonists," "anti-opioids," "antiopiates," "opiates having antagonist activity" and "antagonists" are meant to refer to opioid-like substances that bind to opioid receptors, but produce little or no agonist activity.

As used herein, the terms "opiates having κ antagonist activity," "opioids having κ antagonist activity" and "κ antagonists" are meant to refer to opioid-like substances that bind to the κ receptor, but produce little or no agonist activity.

"Pharmaceutically effective modes" are meant to include, but not be limited to, the application of a drug composition as a solution in an innocuous pharmaceutically acceptable solvent, as an emulsion, as a suspension, as a dispersion in suitable carriers, as a patch or in the form of pills, or capsules with solid, liquid or gel carriers, and other such methods well-known in the art. The formulations of this invention may include pharmaceutically acceptable excipients such as stabilizers, anti-oxidants, binders, coloring agents, emulsifiers, and other such excipients well-known in the art. The drugs and drug compositions comprising the agonists and antagonists described above and below, may be administered in any pharmaceutically effective mode.

Opiate antagonists are molecular structures similar to opiates but do not have appreciable direct agonist activity. Antagonists have the ability to reduce or prevent the receptor binding of opiate agonists, thus neutralizing their biologic effect. Anti-opioids, or narcotic antagonists, are characterized by their ability to displace narcotic agonists from the respective receptors. Since most narcotics possess several agonist actions, e.g. $\mu, \delta$, and κ, anti-opioids may possess antagonist capabilities for those (and other) receptors as well. In general, the antagonist activity, or effectiveness of anti-opioids is not equal at the various receptor sites and may vary significantly, often times by more than an order of magnitude. For example, the $\mu$ receptor binding effectiveness for naltrexone is 12 times higher than its effectiveness to bind to a κ receptor, which results in a 12-fold increase of agonist displacement at the $\mu$ receptor over the κ receptor. Since the $\mu$ receptor is known to control (amongst others) euphoria, a suppression of this action 12-fold over any action controlled by κ, e.g. for various metabolic functions can actually result in disphoria, if the antiopioid dosage has to be increased to achieve the desired effect at the κ site.

Metformin hydrochloride is a non-sulfonylurea type antihyperglycemic agent, which improves glucose tolerance in type 2 diabetic subjects, primarily by decreasing hepatic gluconeogenesis and glucose production (Edelman, S.V.: Clinical Diabetes; 16,1:37–40). The major side effects are potential lactic acidosis, and the impact of the required massive therapeutic doses on liver and kidney function. Metformin is, therefore, contraindicated for patients with hepatic and renal insufficiency, which is aggravated by the fact that a typical daily dose ranges between 1,500 and 2,500 mg.

During the investigations into, and development of, non-addictive morphine based analgesics, typically requiring a combination of agonistic and antagonistic actions at various opiate receptor sites, i.e. $\mu$, $\delta$ and κ receptors, a variety of so-called 'pure' antagonists have evolved as by-products, and some of these narcotic antagonists, or anti-opioids, have been shown to have potential in the treatment of a variety of disease conditions.

U.S. Pat. No. 4,272,540 discloses various 14-methoxy substituted 3-hydroxy or 3-methoxy-6-one morphinans, which are variously useful as analgesics, narcotic antagonists, and mixed analgesics and narcotic antagonists.

U.S. Pat. No. 4,451,470 discloses 14-fluoromorphinans which are useful as analgesic, narcotic antagonists and/or anorexigenic agents.

U.S. Pat. No. 4,478,840 discloses 17-cycloalkylmethyl-4,-5α-epoxymorphinan-3,14-diol compounds useful for suppression of appetite in mammals.

U.S. Pat. No. 4,619,936 discloses pharmaceutical compositions containing (5α,6α)7,8-didehydro-4,5-epoxy-17-(2-propanyl)-morphinano-3,6-diol for the purpose of appetite reduction.

U.S. Pat. No. 4,882,335 discloses a method useful as an adjunct in the treatment of alcoholism. The method involves having the patient drink alcoholic beverages, while an opiate antagonist blocks the positive reinforcement effects of ethanol in the brain.

U.S. Pat. No. 5,086,058 discloses a method for treating alcoholism. The method involves having the patient drink alcoholic beverages while nalmefene, an opiate antagonist, blocks the positive reinforcement effects of ethanol in the brain.

In order to address the dramatic increases in diabetes, obesity and other CHDRFs, and their effects on patient morbidity/mortality and national health care expenditures, the focus of pharmaceutical research is shifting from post symptomatic stabilization to prevention and intervention. The pathophysiology of the syndrome CHDRFs is a progressive process with changing conditions, as physiologic control functions become strained, exhausted and, eventually, supplemented or replaced by other compensatory mechanisms. Therefore, the different stages in this progression necessitate different interventive measures tailored to retain or restore those functions still viable.

U.S. Pat. No. 5,727,570 discloses a method of treatment of humans suffering from hyperlipidemia by administering a drug composition selected from a group consisting of opiate antagonists and drugs which substantially equally reduce the amount of catecholamines bound to catecholamine binding sites. In a model case study, conducted with a pure antiopioid, this method was applied during the pre-diabetic stage of IFG combined with IR, and resulted in significant improvements in all carbohydrate and lipid control functions, restoring all relevant Blood Analyte Concentrations (BAC) to normal physiologic levels, with a reduction of FBG to 95 mg/dL.

U.S. Pat. No. 5,878,750 discloses a method of treating humans suffering from the Coronary Heart Disease Risk Factor syndrome by administering a drug composition selected from the group of opiate antagonists or anti-opioids and drugs which substantially equally reduce the amounts of catecholamines bound to all catecholamine binding sites. A model case study involved the administration of a pure opioid antagonist to an overweight subject with early stage Type 2 Diabetes and dislipidemia, having a fasting blood glucose level (FBG) of 138 mg/dL, which is exceeding the criteria for IFB and IGT. Although all carbohydrate and lipid metabolism related BACs, as well as overweight and hypertension, showed significant improvements, all were restored back to normal, with the exception of FBG which, despite its 13% improvement, only dropped from 138 mg/dL to 120 mg/dL, still within the IGT range.

U.S. Pat. No. 6,026,817 discloses a method of treatment of humans suffering from the syndrome of Coronary Heart Disease Risk Factors which comprises the steps of 1) administering a priming dose of a drug composition selected from the group consisting of opioid antagonists and 2) administering a maintenance dose of said drug. It also discloses a method of combining said dosing sequence with a method of improving the balance between or equalizing the IC-50 values of an anti-opioid composition for its respective target receptors, by adding small amounts of one or more drugs with opioid agonist activity whereby the agonist competes with the antagonist for the particular receptor, and diminishes, but does not totally remove any of the respective antagonist properties of the anti-opioid composition.

The present invention provides an improved method of treating the Syndrome of CHD risk factors, by combining the method of treating this syndrome with anti-opioids, with a method for treating the early morning rise in GNG by the administration of a μ agonist. The syndrome of CHD risk factors includes the various disease states of Type 2 Diabetes, as well as hyper- or dislipidemia, overweight, obesity and/or essential hypertension. The disease states of the Type 2 Diabetes syndrome progress through insulin resistance (IR), impaired fasting glucose (IFG), excessive hepatic gluconeogenesis (GNG) and glucose production (GP), and impaired glucose tolerance (IGT) to the clinical form of Type 2 Diabetes. The method provides a treatment for any number of individual conditions within the syndromes of CHDRF and Type 2 Diabetes. This invention also provides a method of treating the early morning increase in gluconeogenesis and increased glucose production which, in the presence of relatively impaired insulin secretion, results in elevated fasting glucose levels. This invention further provides a method to restore the physiologic acute, first phase insulin release. Another aspect of this invention is to provide an improved first pass insulinization of the liver, resulting in a restoration of enzyme functions involved in hepatic fuel processing, including carbohydrate oxidation and storage.

Drugs which are useful in the methods of the present invention, i.e. methods for treating humans suffering from CHD risk factors, include opioid drug compositions with centrally or peripherally acting μ agonist activity in combination with centrally acting compositions of non-selective or selective opioid antagonists. Although the μ opioid agonist drug composition can be administered at times different from the administration of the compositions of the opioid antagonists, it is preferred to administer the combination of both at the same time in order to facilitate the matching of their respective pharmnacodynamics.

Bi-directional effects of opioids are known to exist, in particular between μ and κ agonists, such as μ agonists producing euphoria and κ agonists producing the opposite, namely disphoria. Conversely, μ antagonists can antagonize euphoria and enhance the effect of the κ agonist, while the κ antagonist can produce or enhance euphoria. Examples of this phenomenon also include the opposing effects of μ and κ opiates in motivational processes (Herz A.: NIDA Res Monogr 90:17–26), or in opioid reward mechanisms (Herz A.: Can J Physiol Pharmacol 76,3:252–8), and other μ-opposing actions of the κ-opioid receptor (Pan Z. Z.: Trends Pharmacol Sci; 19,3:94–8).

Opioids having selective or predominant κ-antagonist activity include, but are not limited to nalmefene, naltrexone, nor-binaltorphine, (Portoghese, P. S., Lipkowski, A. W., Takemori, A. E.; Life Sciences 40:1287–92); guanidylated naltrindole (GNTI), (Jones R. M., Hjorth, A. S., Schwartz, T. W., and Portoghese, P. S.; Journal of Medicinal Chemistry 41,25:4911–4), (-)-(1R,5R,9R)-5,9-diethyl-2-(3-furylmethyl)-2-hydroxy-6,7-benzomorphan (MR 2266) (Merz, H., Langbein, A., Stockhaus, K., Walther, G., & Wick, H.; Advances in biochemical psychopharmacology, Vol 8:91–107), a triethylenedioxy derivative of naltrexamine (TENA), (Portoghese, P. S., Takemori, A. E.; Life Sciences 36: 801–5) and buprenorphine.

Opioids having selective or predominant μ agonist activity include, but are not limited to, dihydromorphine, morphine, hydromorphone, methadone, fentanyl, sufentanyl, buprenorphine, demorphine, codeine, ethylmorphine, etonitazene, hydrocodone, levorphanol, norcodeine, normorphine, loperamide, {D-Ala$^2$-N-Me-Phe$^4$-Gly$^5$-ol)-Enkephalin} (DAMGO) and oxycodone. Most opioids pass the Blood Brain Barrier (BBB) and are, therefore both, centrally and peripherally active, i.e. they can act upon CNS sites as well as peripheral sites, such as the gut and hormone producing glands, including the endocrine pancreas and the adrenal medulla. Some opioids, e.g. loperamide, do not pass the BBB and are, therefore, only peripherally active with little or no CNS effect. Since drug addiction generally requires a central effect, peripherally acting opioid agonists are typically not addictive and generally not 'scheduled' as narcotics.

Buprenorphine is a mixed agonist-antagonist having high affinity at the μ opiate receptor with partial agonist activity, and at the κ receptor with antagonist activity. Because of its κ receptor antagonist activity and low partial κ activity it will produce minimal and perhaps clinically insignificant physical dependence. Bupreprohine has been used as an effective analgesic for the treatment of moderate to severe pain and of opioid dependence. (Lewis J. W.: Drug and Alcohol Dependence; 14:363–372). Elevations in cortisol and glucose, caused by surgical stress, have been observed to decline following the administration of buprenorphine to treat analgesia during and following total hip replacement (McQuay H. J. et. al.: Br J Anaesth; 52:1013–19).

Loperamide is a synthetic opioid used for the treatment of diarrhea, which is more effective and safe than other opioid drugs in the treatment of diarrhea of various causes (Ruppin H: Acta Physiol Scand; 127,3:275–9) Loperamide is a 'non-scheduled' opioid with μ agonist activity as opposed to most other opioid agonists which are listed as 'controlled substances.' Loperamide is reported to raise blood glucose concentrations at dose levels required for the acute treatment of diarrhea (Caldara R. et. al.: Eur J Clin Pharmacol; 21,3:185–8), and has been used in the "Loperamide test":a simple and highly specific screening test for hypercortisolism in children and adolescents" (Buzi F. et. al.: Acta Paediatr; 86,11:1177–80).

The invention results in an improved method of treating coronary disease risk factors and an improvement toward normal values of fasting blood glucose, C-peptide, fasting total cholesterol, fasting LDL-cholesterol, fasting HDL-cholesterol, LDL/HDL ratio, fasting TG, fasting FFA, body weight, systolic blood pressure and/or diastolic blood pressure.

EXAMPLE

The examples are being described for purely illustrative purposes, and are in no way meant to limit the scope of the invention.

The daily blood glucose profile of a 71 year old subject with early stage Type 2 Diabetes and dislipidemia was monitored on four different occasions. For each occasion, the glucose profile of the subject was monitored for one day after a different treatment had been administered. Sufficient time intervals were allowed between treatments to eliminate any carry-over effect from earlier treatment methods.

The four different treatments are described below. The blood glucose (BG) of the man was measured in mg/dL at the time intervals listed below. This data compiled below has been graphed in FIG. 1.

Treatment 1

○- no drug treatment.
Breakfast: 08:40–09:00; lunch: 12:25–12:50; dinner: 18:40–19:00

| time [h]   | 08:10 | 10:00 | 12:20 | 14:00 | 18:30 | 20:00 |
|------------|-------|-------|-------|-------|-------|-------|
| BG [mg/dL] | 132   | 156   | 104   | 150   | 98    | 117   |

Treatment 2

■-850 mg metformin administered orally at 08:10.
Breakfast: 08:40–09:00; lunch: 12:20–12:40; dinner: 19:10–19:30

| time [h]   | 08:10 | 09:45 | 12:30 | 14:00 | 19:00 | 20:55 |
|------------|-------|-------|-------|-------|-------|-------|
| BG [mg/dL] | 122   | 146   | 106   | 129   | 90    | 112   |

Treatment 3

▲- 850 mg metforrnin administered orally at 08:20, plus 0.5 mg loperamide, a $\mu$-agonist, administered orally at dinner the preceding day.
Breakfast: 08:40–09:00; lunch: 11:55–12:15; dinner: 18:25–18:45

| time [h]   | 08:20 | 09:50 | 10:30 | 12:05 | 13:00 | 18:15 | 20:20 |
|------------|-------|-------|-------|-------|-------|-------|-------|
| BG [mg/dL] | 118   | 131   | 126   | 107   | 125   | 85    | 115   |

Treatment 4

▼- 0.1 mg loperamide, a $\mu$-agonist, administered orally at 20:00 the preceding day.
Breakfast: 08:20–08:40; lunch: 13:00–13:20; dinner: 20:00–20:20

| time [h]      | 07:55 | 08:40 | 09:20 | 09:50 | 10:20 | 13:00 | 13:25 | 14:05 | 15:15 | 17:50 | 18:30 | 19:35 | 20:20 |
|---------------|-------|-------|-------|-------|-------|-------|-------|-------|-------|-------|-------|-------|-------|
| BG [mg/dL]    | 107   | 105   | 115   | 99    | 105   | 100   | 97    | 111   | 102   | 93    | 87    | 113   | 88    |

FIG. 1 and the supporting data demonstrate that post prandial peaks in glucose concentration are reduced with the administration of 850 mg of metformin, i.e. by selectively reducing gluconeogenesis (-■-). In addition, supplementing administration of metformin with the administration of a $\mu$-agonist, such as loperarnide, not only reduces the post prandial glucose peaks, but also lowers the fasting glucose concentration as well (-▲-). The most significant reduction of a post prandial glucose peak occurs after breakfast. The data also demonstrate the ability of $\mu$-agonists, in suitable dose ranges, to effectively reduce GNG and GP. Of particular significance is the data produced with the administration of the $\mu$-agonist alone (-▼-). It demonstrates a highly significant reduction in fasting, pre- and post prandial blood glucose values by effectively reducing GNG and GP. The administration of the $\mu$-agonist also results in very significant increases in first phase insulin release, as can be derived from the pronounced decreases of blood glucose concentrations throughout the intake of the meals, and from the reduced duration and excursions of the post-prandial peaks, compared to placebo and metformin.

Type 2 Diabetes, IGT, overweight and obesity are associated with defective or lacking first phase insulin release, as is Type 1 Diabetes. In contrast to Type 1 Diabetes, all these afflictions, except late stage Type 2 Diabetes, retain second, proportional phase insulin secretory capacity. The restoration of hepatic carbohydrate oxidation and storage in Type 1 Diabetics requires appropriately controlled exogenous insulin infusions.

According to the present invention, such restoration of hepatic carbohydrate oxidation storage in subjects afflicted with the CHD risk factors is achieved by administration of the $\mu$-agonist and κ-antagonists, or a combination thereof. Drug compositions useable in the present invention may be single substances or may also be any combination of opioid agonists, antagonists or mixed agonist/antagonists.

The effective dose of the $\mu$-agonist loperamide is less than 0.5 mg per day, or smaller by more than an order of magnitude than the typical dose required for the treatment of diarrhea. The effective dose for other $\mu$-agonists, or single- or multi-molecular mixed $\mu$-agonist/κ-antagonist compositions may vary depending upon factors such as receptor binding, the absorption rate, bio-availability, excretion rate and the rate of metabolism of the drug. The preferred method of administration is in a timed release format, administered before dinner, or before the onset of the early rise in GNG and GP.

What is claimed is:

1. A method of treating a human suffering from one or more conditions included within the Coronary Heart Disease Risk Factor (CHDRF) syndrome, the method comprising administering, by a pharmaceutically effective mode, a drug composition having an active ingredient which is an opiate having $\mu$ agonist activity.

2. The method of claim 1, wherein the opiate having $\mu$ agonist activity comprises a single molecular entity.

3. The method of claim 1, wherein the opiate having $\mu$ agonist activity comprises a combination of molecular entities.

4. The method of claim 1, wherein the drug composition comprises a peripherally acting $\mu$ agonist.

5. The method of claim 4, wherein the drug composition is loperamide.

6. The method of claim 1, wherein the drug composition comprises a centrally acting $\mu$ agonist.

7. The method of claim 1, wherein the drug composition further comprises an opiate having mixed $\mu$ agonist and κ antagonist activity.

8. The method of claim 7, wherein the opiate having mixed $\mu$ agonist and κ antagonist activity is buprenorphine.

9. The method of claim 1 wherein the drug composition includes at least one of the following:
   i) dihydromorphine;
   ii) morphine;
   iii) hydromorphone;
   iv) methadone;
   v) fentanyl;
   vi) sufentanyl;
   vii) buprenorphine;
   viii) demorphine;
   ix) codeine;
   x) ethylmorphine;

xi) etonitazene;
xii) hydrocodone;
xiii) levorphanol;
xiv) norcodeine;
xv) normophine;
xvi) (D-Ala$^2$-N-Me-Phe$^4$-Gly$^3$-ol)-Enkephalin (DAMGO); and
xvii) oxycodone.

10. The method of claim 1, wherein the drug composition includes at least one of the following:
   i) nalmefene;
   ii) naltrexone;
   iii) nor-binaltorphine;
   iv) (-)-(1R,5R,9R)-5,9-diethyl-2-(3-furylmethyl)-2-hydroxy-6,7-benzomorphan (MR 2266);
   v) a triethylenedioxy derivative of B-naltrexamine (TENA); and
   vi) guanidylated naltrindole (GNTI).

11. The method of claim 1, wherein the condition included within the CHDRF Syndrome is Type 2 Diabetes.

12. The method of claim 1, wherein the condition included within the CHDRF Syndrome is Impaired Fasting Glucose (IFG).

13. The method of claim 1, wherein the condition included within the CHDRF syndrome is Impaired Glucose Tolerance (IGT).

14. The method of claim 1, wherein the condition included within the CHDRF syndrome is overweight.

15. The method of claim 1, wherein the condition included within the CHDRF syndrome is obesity.

16. The method of claim 1, wherein the condition included within the CHDRF syndrome is dislipidemia.

17. The method of claim 1, wherein the drug composition further comprises an opiate antagonist.

18. The method of claim 17, wherein the opiate antagonist is an opiate having κ antagonist activity.

19. A method of treating a human suffering from one or more conditions included within the Coronary Heart Disease Risk Factor (CHDRF) syndrome, the method comprising administering, by a pharmaceutically effective mode, a drug composition having an active ingredient which is a combination of an opiate antagonist and an opiate having μ agonist activity.

20. The method of claim 19, wherein the opiate antagonist comprises a single molecular entity.

21. The method of claim 19, wherein the opiate antagonist comprises a combination of molecular entities.

22. The method of claim 19, wherein the opiate having μ agonist activity comprises a single molecular entity.

23. The method of claim 19, wherein the opiate having μ agonist activity comprises a combination of molecular entities.

24. The method of claim 19, wherein the drug composition comprises a peripherally acting μ agonist.

25. The method of claim 24, wherein the drug composition is loperamide.

26. The method of claim 19, wherein the drug composition comprises a centrally acting μ agonist.

27. The method of claim 19, wherein the drug composition further comprises opiates having mixed μ agonist and κ antagonist activity.

28. The method of claim 27, wherein the opiate having mixed μ agonist and κ antagonist activity is buprenorphine.

29. The method of claim 19 wherein the drug composition includes at least one of the following:

xviii) dihydromorphine;
xix) morphine;
xx) hydromorphone;
xxi) methadone;
xxii) fentanyl,
xxiii) sufentanyl;
xxiv) buprenorphine;
xxv) demorphine;
xxvi) codeine;
xxvii) ethylmorphine;
xxviii) etonitazene;
xxix) hydrocodone;
xxx) levorphanol,
xxxi) norcodeine;
xxxii) normophine;
xxxiii) (D-Ala$^2$-N-Me-Phe$^4$-Gly$^3$-ol)-Enkephalin (DAMGO); and
xxxiv) oxycodone.

30. The method of claim 19, wherein the drug composition includes at least one of the following:
   v) nalmefene;
   vi) naltrexone;
   vii) nor-binaltorphine;
   viii) (-)-(1R,5R,9R)-5,9-dietbyl-2-(3-furylnethyl)-2-hydroxy-6,7-benzomorphan (MR 2266);
   v) a triethylenedioxy derivative of B-naltrexamine (TENA); and
   vi) guanidylated naltrindole (GNTI).

31. The method of claim 19, wherein the condition included within the CHDRF Syndrome is Type 2 Diabetes.

32. The method of claim 19, wherein the condition included within the CHDRF Syndrome is Impaired Fasting Glucose (IFG).

33. The method of claim 19, wherein the condition included within the CHDRF syndrome is Impaired Glucose Tolerance (IGT).

34. The method of claim 19, wherein the condition included within the CHDRF syndrome is overweight.

35. The method of claim 19, wherein the condition included within the CHDRF syndrome is obesity.

36. The method of claim 19, wherein the condition included within the CHDRF syndrome is dislipidemia.

37. The method of claim 19, wherein the opiate antagonist is an opiate having κ antagonist activity.

38. The method of claim 19, wherein the condition included within the CHDRF syndrome is impaired fuel processing.

39. The method of claim 38, wherein the impaired fuel processing includes control of carbohydrate oxidation and storage.

40. The method of claim 19, wherein in the condition included within the CHDRF Syndrome is excessive gluconeogenesis (GNG).

41. The method of claim 19, wherein the condition included within the CHDRF Syndrome is excessive endogenous glucose production (GP).

42. The method of claim 19, wherein the condition included within the CHDRF Syndrome is impaired first phase β-cell insulin secretion.

* * * * *